US010226443B2

(12) United States Patent
Scher et al.

(10) Patent No.: US 10,226,443 B2
(45) Date of Patent: Mar. 12, 2019

(54) METHODS FOR TREATING PSORIATIC ARTHRITIS

(71) Applicants: Jose U. Scher, Jersey City, NJ (US); Carles Ubeda, Valencia (ES); Dan R. Littman, New York, NY (US); Eric G. Pamer, Guilford, CT (US); Steven B. Abramson, Rye, NY (US); Sergei B. Koralov, Millburn, NJ (US)

(72) Inventors: Jose U. Scher, Jersey City, NJ (US); Carles Ubeda, Valencia (ES); Dan R. Littman, New York, NY (US); Eric G. Pamer, Guilford, CT (US); Steven B. Abramson, Rye, NY (US); Sergei B. Koralov, Millburn, NJ (US)

(73) Assignees: New York University, New York, NY (US); Memorial Sloan-Kettering Cancer Center, New York, NY (US); Fundacion Para El Fomento De La Investigacion Sanitaria Y Biomedica De La Comunitat Valenciana (Fisabio), Valencia (ES)

( * ) Notice: Subject to any disclaimer, the term of this patent is extended or adjusted under 35 U.S.C. 154(b) by 0 days.

(21) Appl. No.: 14/885,084

(22) Filed: Oct. 16, 2015

(65) Prior Publication Data
US 2016/0136122 A1 May 19, 2016

Related U.S. Application Data

(60) Provisional application No. 62/064,733, filed on Oct. 16, 2014.

(51) Int. Cl.
| | | |
|---|---|---|
| A61K 31/20 | (2006.01) | |
| A61K 31/19 | (2006.01) | |
| A61K 35/74 | (2015.01) | |
| A61K 45/06 | (2006.01) | |

(52) U.S. Cl.
CPC ............. *A61K 31/20* (2013.01); *A61K 31/19* (2013.01); *A61K 35/74* (2013.01); *A61K 45/06* (2013.01)

(58) Field of Classification Search
CPC ........ A61K 31/20; A61K 45/06; A61K 35/74; A61K 31/19
See application file for complete search history.

(56) References Cited

U.S. PATENT DOCUMENTS 5,175,190 A * 12/1992 Burton .................. A61K 31/20
514/560

OTHER PUBLICATIONS

Quigley (Gastroenterology & Hepatology, 2013, vol. 9, issue 9, pp. 560-569).*
Sommer et al (Nature Review—Microbiology, 2013, vol. 11, pp. 227238).*
Cua et al., "Gut microbiota strikes back", Nat Med, 2011, 17:1055-6.
Van Praet et al. "Mucosal inflammation in spondylarthritides: past, present, and future", Curr Rheumatol Rep 2011, 13:409-15.
Sherlock et al. "IL-23 induces spondyloarthropathy by acting on ROR-gammat+CD3+CD4-CD8-entheseal resident T cells", Nat Med, 2012, 18:1069-76.
Van Praet et al. "Microscopic gut inflammation in axial spondyloarthritis: a multiparametric predictive model", Ann Rheum Dis, 2013, 72:414-7.
Rath et al., "Normal luminal bacteria, especially Bacteroides species, mediate chronic colitis, gastritis, and arthritis in HLA-B27/human beta2 microglobulin transgenic rats", J Clin Invest, 1996, 98:945-53.
Ruutu et al., "Beta-glucan triggers spondylarthritis and Crohn's disease-like ileitis in SKG mice", Arthritis Rheum, 2012, 64:2211-2222.
Manichanh et al., "Reduced diversity of faecal microbiota in Crohn's disease revealed by a metagenomic approach", Gut, 2006, 55:205-211.
Png et al., "Mucolytic bacteria with increased prevalence in IBD mucosa augment in vitro utilization of mucin by other bacteria", Am J Gastroenterol, 2010,105:2420-8.
Vigsnaes et al., "Gram-negative bacteria account for main differences between faecal microbiota from patients with ulcerative colitis and healthy controls", Benef Microbes, 2012, 3:287-97.
Rajilic-Stojanovic et al., "Phylogenetic analysis of dysbiosis in ulcerative colitis during remission", Inflamm Bowel Dis, 2013;19:481-8.
Willing et al., "A pyrosequencing study in twins shows that gastrointestinal microbial profiles vary with inflammatory bowel disease phenotypes", Gastroenterology, 2010, 139:1844-1854.
Morgan et al., "Dysfunction of the intestinal microbiome in inflammatory bowel disease and treatment", Genome Biol 2012, 13:R79.
Joossens et al., "Dysbiosis of the faecal microbiota in patients with Crohn's disease and their unaffected relatives", Gut 2011;60:631-7.
Smith et al., "The microbial metabolites, short-chain fatty acids, regulate colonic Treg cell homeostasis", Science, 2013, 341:1-10.
Garner et al., "Volatile organic compounds from feces and their potential for diagnosis of gastrointestinal disease", FASEB J, 2007, 21:1675-88.
De Preter et al., "Faecal metabolite profiling identifies medium-chain fatty acids as discriminating compounds in IBD", Gut 2015, 64:447-458.
Liberato et al., "Medium chain fatty acids are selective peroxisome proliferator activated receptor (PPAR) gamma activators and pan-PPAR partial agonists", PLoS One , 2012, 7:e36297.
Bassaganya-Riera et al., "Probiotic bacteria produce conjugated linoleic acid locally in the gut that targets macrophage PPAR gamma to suppress colitis", PLoS One, 2012, 7:e31238.
Bassaganya-Riera et al., "Conjugated linoleic acid modulates immune responses in patients with mild to moderately active Crohn's disease", Clin Nutr 2012; 31:721-7.
Chandran et al., "Soluble biomarkers differentiate patients with psoriatic arthritis from those with psoriasis without arthritis", Rheumatology, 2010; 49:1399-1405.

(Continued)

*Primary Examiner* — Sudhakar Katakam
(74) *Attorney, Agent, or Firm* — Hoffmann & Baron, LLP

(57) ABSTRACT

Methods, agents and compositions thereof for treating psoriatic arthritis (PsA) are encompassed herein.

6 Claims, 5 Drawing Sheets

(56) References Cited

OTHER PUBLICATIONS

You et al., "Effects of Medium-Chain Triglycerides, Long-Chain Triglycerides, or 2-Monododecanoin on Fatty Acid Composition in the Portal Vein, Intestinal Lymph, and Systemic Circulation in Rats", JPEN J Parenter Enteral Nutr., 2008, 32:169-175.

Ereaux et al., "The oral administration of undecylenic acid in the treatment of psoriasis", Canad. M. A. J., 1949, 61:361-364.

Papada et al., "Anti-inflammatory effect of elemental diets with different fat composition in experimental colitis", British Journal of Nutrition, 2014, 111:1213-1220.

Kim et al., "A Medium-Chain Fatty Acid, Capric Acid, Inhibits RANKL-Induced Osteoclast Differentiation via the Suppression of NF-kappaB Signaling and Blocks Cytoskeletal Organization and Survival in Mature Osteoclasts", Mol. Cells 2014, 37:598-604.

Park et al., "Capric Acid Inhibits NO Production and STAT3 Activation during LPS-Induced Osteoclastogenesis", PLoS One, 2011, 6, Issue 11, e27739.

Hoshimoto et al., "Caprylic acid and medium-chain triglycerides inhibit IL-8 gene transcription in Caco-2 cells: comparison with the potent histone deacetylase inhibitor trichostatin A", British Journal of Pharmacology, 2002, 136: 280-286.

Maslowski et al., "Regulation of inflammatory responses by gut microbiota and chemoattractant receptor GPR43", Nature, 2009, 461:1282-1286.

Jensen et al., "Intestinal absorption of octanoic, decanoic, and linoleic acids: effect of triglyceride structure", Ann Nutr Metab, 1994, 38:104-116.

\* cited by examiner

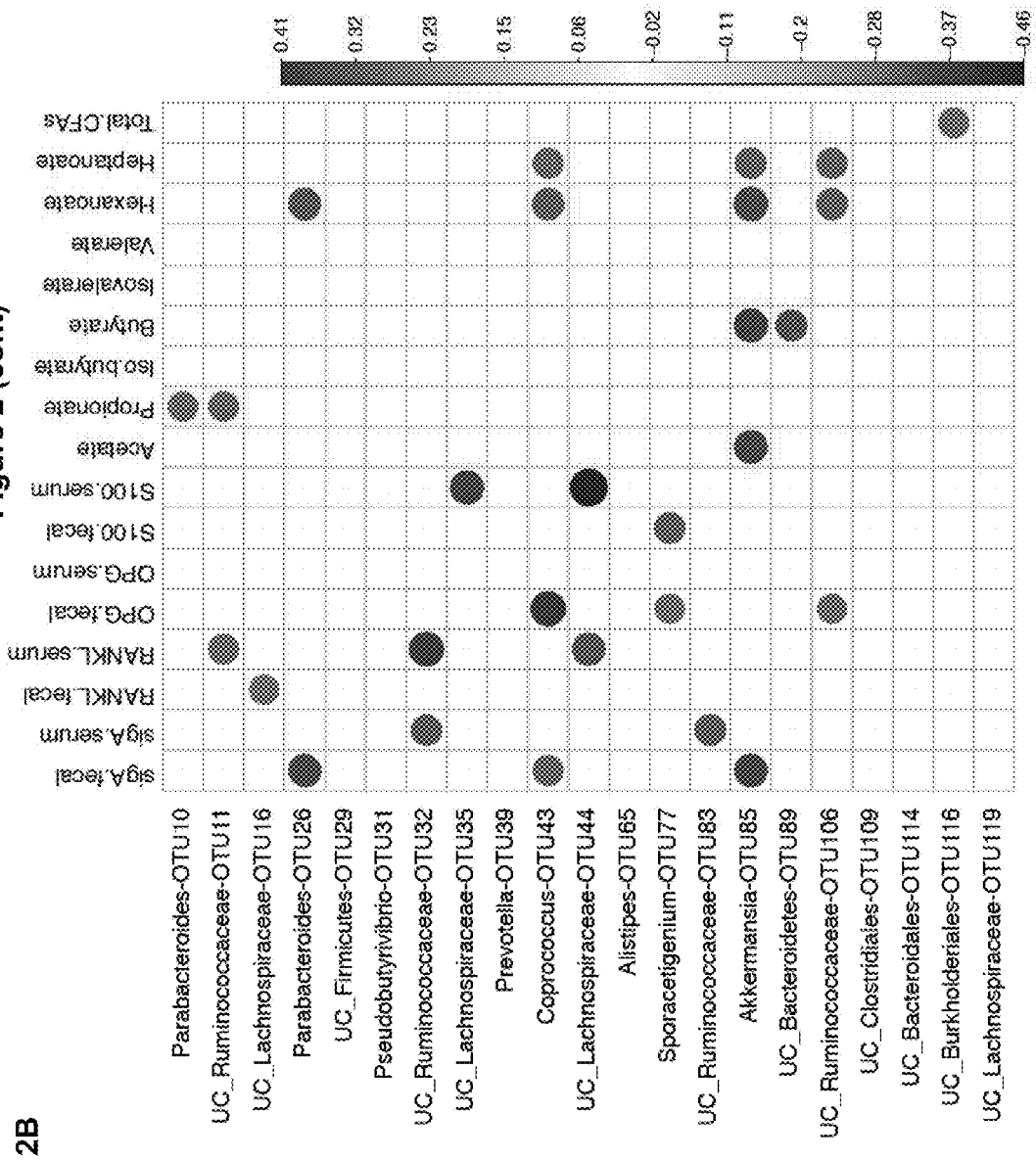

METHODS FOR TREATING PSORIATIC ARTHRITIS

CROSS REFERENCE TO RELATED APPLICATIONS

This application claims priority under 35 USC § 119(e) from U.S. Provisional Application Ser. No. 62/064,733, filed Oct. 16, 2014, which application is herein specifically incorporated by reference in its entirety.

GOVERNMENTAL SUPPORT

The research leading to the present invention was supported, at least in part, by RC2 AR058986 and K23AR064318 from the National institute of Arthritis and Musculoskeletal and Skin Diseases. Accordingly, the Government has certain rights in the invention.

FIELD OF THE INVENTION

Therapeutic, diagnostic, and prognostic methods pertaining to psoriatic arthritis (PsA) are described herein. Compositions for use in such methods are also set forth herein.

BACKGROUND OF THE INVENTION

Spondylarthritides (SpA) are disabling rheumatic diseases that present mainly with inflammation of the axial skeleton, peripheral joints, and tendons. PsA is a type of chronic SpA, typically affecting individuals with pre-existing psoriasis of the skin (Ps). Psoriasis is a chronic, genetically based, immune-mediated inflammatory disorder affecting 2%-3% of the Caucasian population in western countries (Nestle et al. N Engl J Med 361:496-509, 2009). Psoriasis plaques may be localized or widespread across the body, and fingernails and toenails are frequently involved (Puig et al. Clinicoecon Outcomes Res. 6: 93-100, 2014).

PsA has been defined as a unique inflammatory arthritis associated with psoriasis. It is viewed as a complex disease in which environmental, host, and random factors coalesce, leading to disease in genetically susceptible individuals (Gladman et al. Ann Rheum Dis. 64(Suppl 2): ii14-ii17, 2005; Queiro et al. ISRN Dermatol. 2014; 2014: 570178.). PsA is associated with significant morbidity and mortality and is estimated to incur costs equivalent to those of rheumatoid arthritis (Zink et al. Journal of Rheumatology 33:86-90, 2006). Despite recent advances in diagnosis and treatment, however, the pathogenesis of PsA remains unclear. Previously proposed environmental factors that may trigger disposition to or development of PsA include viruses, vaccinations, bacterial infections, trauma and stress.

In view of the above, new methods for use in the accurate diagnosis, prognosis, monitoring, and/or treatment of patients with PsA are urgently needed. Methods described herein address these needs.

The citation of references herein shall not be construed as an admission that such is prior art to the present invention.

SUMMARY OF THE INVENTION

The present inventors have characterized the abundance and diversity of gut microbiota in patients with never-treated, new-onset psoriatic arthritis (PsA). To achieve this end, high-throughput 16S rRNA pyrosequencing was utilized to compare community composition of gut microbiota in PsA patients (n=16), subjects with psoriasis of the skin (Ps) (n=15) and healthy, matched-controls (n=17). Samples from patients with PsA, psoriasis of the skin (Ps), new-onset rheumatoid arthritis (NORA), and healthy controls were also assessed for the presence and levels of various fatty acids.

As described in detail herein, gut microbiota observed in PsA and Ps patients was less diverse when compared to healthy controls. These microbial differences were attributed to the reduced presence of several taxa in the PsA intestinal microbiota. While both groups showed a relative decrease in *Coprococcus* species, PsA samples were characterized by a significant reduction in the following bacterial genera: *Akkermansia, Ruminococcus, Pseudobutyrivibrio, Coprobacillus*, Unclassified (UC)_*Clostridia, Verrucomicrobiae, Verrucomicrobia*, and *Verrucomicrobiales*. Fatty acid analysis of fecal samples, furthermore, revealed relatively low levels of hexanoate and heptanoate in PsA and Ps patients.

In an aspect of the present discoveries, a method for treating a subject afflicted with psoriatic arthritis is presented, the method comprising administering to the subject a therapeutically effective amount of at least one by-product of a bacterial species of a genera of *Akkermansia, Ruminococcus, Pseudobutyrivibrio, Coprococcus, Coprobacillus*, Unclassified (UC)_*Clostridia, Verrucomicrobiae, Verrucomicrobia*, and *Verrucomicrobiales* or a composition thereof, wherein administering the therapeutically effective amount of the at least one by-product or composition thereof treats the subject afflicted with psoriatic arthritis. In a more particular embodiment, the subject afflicted with psoriatic arthritis exhibits psoriasis of the skin associated with: pain, swelling, or stiffness in one or more joints, joints that are red or warm to the touch, sausage-like swelling in the fingers or toes (i.e., dactylitis), pain in and around the feet and ankles, especially tendinitis in the Achilles tendon or Plantar fasciitis in the sole of the foot, or lower back pain (i.e. in the area of the sacrum or sacroiliitis); and does not exhibit abdominal pain, vomiting, diarrhea, rectal bleeding, severe pelvic cramps and/or weight loss (symptoms characteristic of IBD and present to the degree observed in IBD).

In a particular aspect, the at least one by-product of the bacterial species is a medium-chain fatty acid (MCFA). Exemplary medium-chain fatty acids include hexanoic acid, heptanoic acid, octanoic acid, decanoic acid, and dodecanoic acid which may be administered singly or in combination. Esters/salts and derivatives of the respective MCFAs are also envisioned for use in accordance with methods described herein. In a particular embodiment, the at least one by-product or composition thereof is formulated to be administered orally or anally (e.g., into at least one of the terminal ileum and right colon). In a more particular embodiment, anal administration of at least one MCFA or an ester/salt or derivative thereof or a composition thereof is performed after colonoscopic irrigation.

In another particular aspect, the at least one by-product of the bacterial species is a short-chain fatty acid (SCFA). Exemplary short-chain fatty acids include acetic acid, butyric acid, iso-butyric acid, propionic acid, valeric acid, and iso-valeric acid, which may be administered singly or in combination. Esters/salts and derivatives of the respective SCFAs are also envisioned for use in accordance with methods described herein. In a particular embodiment, the at least one by-product or composition thereof is formulated to be administered orally or anally (e.g., into at least one of the terminal ileum and right colon). In a more particular embodiment, anal administration of at least one SCFA or an ester/salt or derivative thereof or a composition thereof is performed after colonoscopic irrigation.

In a further aspect, the at least one by-product of the bacterial species is a combination of at least one MCFA and at least one SCFA. Combinations of at least one exemplary MCFA or an ester/salt or derivative thereof and at least one exemplary SCFA or an ester/salt or derivative thereof are envisioned for use in accordance with methods described herein. In a particular embodiment, the at least one by-product or composition thereof is formulated to be administered orally or anally (e.g., into at least one of the terminal ileum and right colon). Anal administration may be performed following colonoscopic irrigation.

As described herein, decreased bacterial diversity of gut microbiota may be determined by isolating a fecal sample from the subject and processing the fecal sample to generate a fecal bacterial sample; and analyzing microbiota diversity in the fecal bacterial sample using nucleic acid sequencing. The nucleic acid sequencing may be shotgun sequencing.

Also encompassed herein is a composition for treating PsA in a subject, the composition comprising at least one by-product of a bacterial species of a genera of *Akkermansia*, *Ruminococcus*, *Pseudobutyrivibrio*, *Coprococcus*, *Coprobacillus*, Unclassified (UC)_*Clostridia*, *Verrucomicrobiae*, *Verrucomicrobia*, and *Verrucomicrobiales* and a buffer compatible with administration thereof to the subject. In a particular embodiment, the buffer is a sterile manmade physiologically compatible carrier or excipient.

In a particular embodiment, the at least one by-product of the bacterial species is at least one MCFA. In a more particular embodiment, the at least one MCFA is hexanoic acid, heptanoic acid, octanoic acid, decanoic acid, and/or dodecanoic acid. Compositions comprising esters/salts (i.e., hexanoate, heptanoate, octanoate, decanoate, and dodecanoate, respectively) or derivatives of the respective MCFAs are also envisioned.

In another particular embodiment, the at least one by-product of the bacterial species is at least one SCFA. In a more particular embodiment, the at least one SCFA is acetic acid, butyric acid, iso-butyric acid, propionic acid, valeric acid, and/or iso-valeric acid. Compositions comprising esters/salts (i.e., acetate, butyrate, iso-butyrate, propionate, valerate, and iso-valerate, respectively) or derivatives of the respective SCFAs are also envisioned.

In a further embodiment, compositions comprising at least one MCFA or an ester/salt or derivative thereof and at least one SCFA or an ester/salt or derivative thereof are envisioned.

In a particular embodiment thereof, the sterile manmade physiologically compatible buffer is compatible with oral or anal administration. Exemplary buffers compatible with oral administration include sterile manmade solutions that are physiologically compatible such as, for example, sterile normal saline or a sterile saline-based gelatin or matrix. Normal saline is typically defined as a solution of 0.90% weight/volume of NaCl, about 300 mOsm/L or about 9.0 grams NaCl per liter of water. In a particular embodiment, the exemplary buffer comprises fermentable fiber and/or resistant starch and, more particularly, at least one of a Type 1-4 resistant starch. In a particular embodiment, oral administration is achieved using an encapsulated means, wherein the capsule is designed to dissolve or disintegrate in the small and/or large intestine. Exemplary buffers compatible with anal administration comprise sterile manmade solutions that are physiologically compatible such as, for example, normal saline, saline-based gelatin, oleaginous (fatty) bases [e.g., theobroma oil (cocoa butter) and synthetic triglycerides], and water soluble or miscible bases (e.g., glycerinated gelatin and polyethylene glycol polymers).

Other objects and advantages will become apparent to those skilled in the art from a review of the following description which proceeds with reference to the following illustrative drawings.

DETAILED DESCRIPTION

Figure 1:
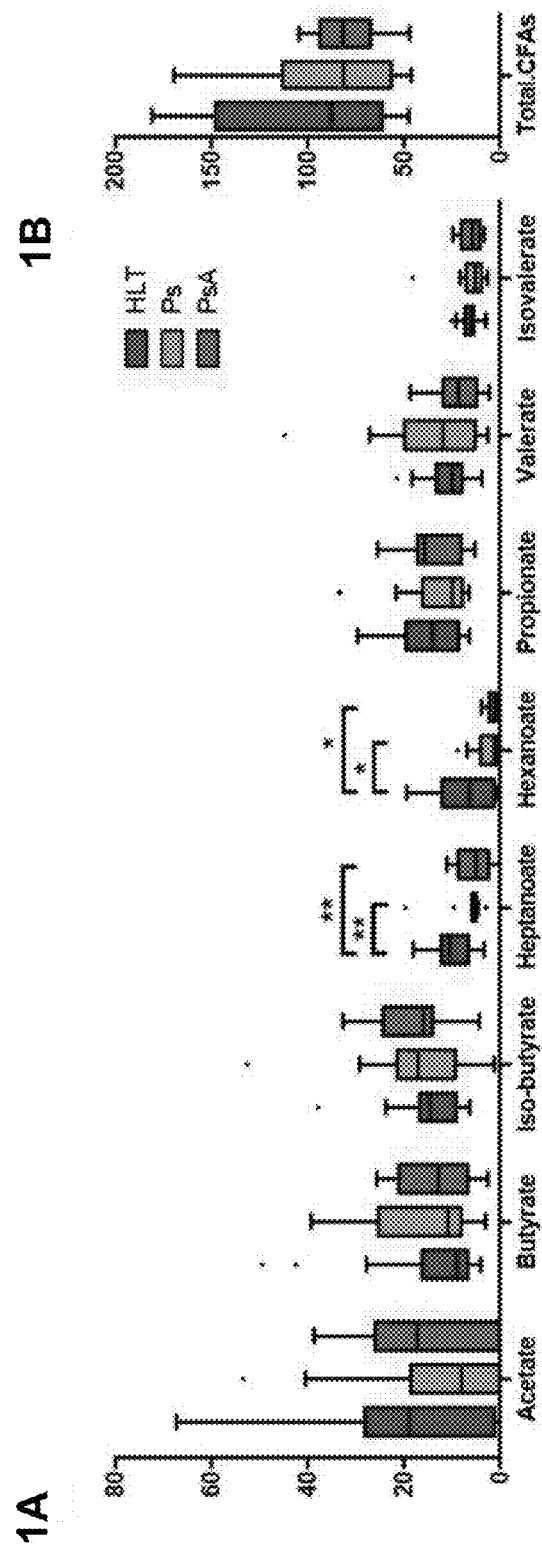
FIGS. 1A and 1B. Fecal levels of short-chain fatty acids (SCFAs) and medium-chain fatty acids (MCFAs). (1A) The levels of SCFAs (Acetate, Butyrate, Iso-Butyrate, Propionate, Valerate, Iso-Valerate) and MCFAs (Hexanoate and Heptanoate) were quantified in fecal samples of all groups. While no differences were found in any of the SCFAs, both MCFAs levels were significantly lower in PsA and Ps samples, compared to healthy controls ($P<0.01$ and $P<0.05$, respectively). (1B) Total levels of fatty acids (CFAs) were similar among groups.

Psoriatic arthritis (PsA) is a type of chronic spondyloarthritis (SpA), typically affecting individuals with pre-existing psoriasis of the skin (Ps). Despite recent advances in diagnosis and treatment, the pathogenesis of PsA remains unclear. The prevalent paradigm posits that in the presence of predisposing genetic factors (e.g., HLA-B*27, Cw6), individuals with Ps will develop PsA after exposure to yet-unidentified environmental factors (1,2). Previously proposed triggers include viruses, bacterial infections, trauma and stress. Interest has recently reemerged concerning the role of the gut microbiome (the totality of bacteria and their genes in a given biological niche) and associated gut inflammation in the pathogenesis of the SpA disease spectrum (3-6). HLA-B27 over-expressing rats, for instance, develop arthritis and colitis only in the presence of specific intestinal microbes (7). Similarly, SKG mice develop joint inflammation, enthesitis, skin inflammation and ileitis after injection with β-glucan, a major component of bacterial and fungal cell walls (8).

Strong epidemiologic evidence also suggests an intimate relationship between intestinal and joint inflammation in SpA. Patients with PsA, Ps and ankylosing spondylitis (AS) experience a much higher incidence of inflammatory bowel disease (IBD). Furthermore, articular manifestations are found in more than one-third of patients with known Crohn's disease or ulcerative colitis (UC) (9). This has led to the consideration of IBD-related arthritis as part of the SpA spectrum.

Several studies have further associated intestinal mucosal inflammation and human SpA. Approximately 70% of all SpA patients show at least some ileocolonoscopic or histologic alterations in the intestinal epithelium. PsA has specifically been shown to be associated with both subclinical gut inflammation (10) and a significantly increased risk of subsequent Crohn's disease (11).

Therefore, several animal and human studies substantiate the hypothesis pointing toward a biological link between (local) gut and (systemic) joint inflammation. This suggests a common etiology, but its precise nature remains unknown.

It is, moreover, noteworthy that although some genetic and environmental features appear to be shared among disorders characterized within the spectrum of spondyloarthrthropathies, many therapeutic approaches are specific to disease phenotype. Etanercept (a TNF-α inhibitor), for example, used for the treatment of Ps and PsA, was supposed to be effective in Crohn's and IBD. However, clinical trials failed to show significant improvement in those patients and etanercept was never approved for this indication by the FDA. Similarly, the new biologic therapies, including usetikinumab (an IL-12/23 blocker) and apremilast (a PDE4 inhibitor), are specifically prescribed for Ps and PsA, but not for IBD, ankylosing spondylitis or reactive arthritis. These, and other examples, are proof that the various disease phenotypes have different pathogenetic pathways that can be targeted through a variety of mechanisms and compounds. Using therapeutic approaches specific to a particular disease phenotype may also benefit from greater pharmacologic specificity, which is generally associated with fewer side effects.

Among sites of exposure to bacterial antigens, the intestinal mucosa represents a unique environment for triggering of local and distal autoimmunity. The human intestinal microbiome contains roughly 100 trillion cells whose genomes encode ~3.3 million protein-coding genes (100-fold more than the human genome). The NIH Human Microbiome Project was recently launched to better understand and define this collective human-microbiome "supraorganism" in both health and disease.

Utilizing novel high-throughput DNA sequencing, it is now possible to identify bacteria in a given community, including unculturable or fastidious organisms, without the need for conventional microbiology techniques. The present study aimed to describe, for the first time, potential alterations in gut microbiota composition of patients with PsA and associated local inflammatory response, compared to Ps and healthy controls.

At the outset, the present inventors set out to characterize the abundance and diversity of gut microbiota in patients with never-treated, new-onset psoriatic arthritis (PsA). Briefly, high-throughput 16S rRNA pyrosequencing was utilized to compare the community composition of gut microbiota in PsA patients and healthy, matched controls. Samples from patients with PsA, psoriasis of the skin (Ps), new-onset rheumatoid arthritis (NORA) and healthy controls were also assessed for the presence and levels of various proteins and bacterial by-products.

As described herein, a total of 48 fecal samples were obtained from PsA, Ps and healthy subjects for sequencing. Using a distance-based similarity of ≥97% for operational taxonomic units (OTU) assignment, a total of 2835 OTUs were identified. These results revealed that microbial diversity was significantly reduced in PsA and Ps samples when compared to healthy subjects, as calculated by the Shannon diversity index and Faith's phylodiversity index. The present inventors also assessed whether the overall structure of the microbiota of healthy samples differed from that of Ps and PsA and quantified the similarity by applying the UniFrac phylogenetic distance. PCoA was further applied to cluster samples along orthogonal axes of maximal variance. PC1 axes determined thereby discriminated most healthy samples from the majority of Ps and PsA samples. Analysis of molecular variance (AMOVA) of the obtained UniFrac distances between samples revealed that overall microbiota structure was also significantly different when comparing PsA to Ps samples.

To investigate further which bacterial taxa were distinct among groups, LefSe analysis was applied (see Methods). Interestingly, while no bacterial taxa were found to be enriched in PsA patients, relative abundance of several microbial clades were decreased in both PsA and Ps, and therefore enriched in healthy controls. Within these identified components of the intestinal microbiota, *Akkermansia, Ruminococcus* and *Pseudobutyrivibrio* were considered the most relevant genera that discriminated PsA microbiota from healthy controls. At other levels of taxonomic classification, unclassified *Clostridia* and the parental taxonomic levels of *Akkermansia* (*Verrucomicrobia, Verrucomicrobiae* and *Verrucomicrobiales*) were also significantly decreased in PsA. The Ps gut microbiota was characterized by a reduced relative abundance of the genera *Parabacteroides* and *Coprobacillus*. The comparison between PsA and Ps groups revealed that the higher taxonomic levels for *Akkermansia* and *Ruminoccocus* (including *Firmicutes/Clostridiales* and *Verrucomicrobiales*, respectively) were significantly less abundant in PsA patients, while *Bacteroidetes* phylum and *Coprobacillus* genus were less abundant in Ps samples. *Akkermansia* and *Ruminoccocus* per se were also relatively decreased in PsA.

Analysis of the microbiota beyond the genus level was undertaken to investigate the various OTUs that were underrepresented in patients with PsA. Several OTUs had a decreased relative abundance compared to healthy controls, including OTUs 43 (*Coprococcus*), 31 (*Pseudobutyrivibrio*), 26 (*Parabacteroides*), 83 (unclassified_Ruminococcaceae), 65 (*Alistipes*), and 85 (*Akkermansia*). Intriguingly, several of these OTUs, including OTU43 as well as OTUs 26, 83, and 35 were also decreased in Ps patients, suggesting a possible common gut microbiota signature for Ps and PsA. Moreover, Ps samples showed a significantly decreased relative abundance of several other OTUs when compared to healthy subjects, including OTUs 44, 89 and 106. OTU11 was the only overrepresented OTU in the Ps group. When comparing PsA and Ps groups, patients with skin disease only had increased relative abundance of OTUs 11, 16 and 32, while patients with PsA had an overrepresentation of OTU44 only.

Changes in gut microbiota can, in turn, alter the milieu of the gut with regard to its metabolite composition. Major categories of metabolites of gut microbiota with relevant biological functions include: a) short- and medium-chain fatty acids (SCFAs and MCFAs) produced by fermentation of dietary carbohydrates, b) choline and L-carnitine metabolites (e.g., trimethylamine (TMA) and betaine), and c) other lipids including conjugated fatty acids and cholesterol.

To explore the potential for alterations in the levels of bacterial by-products in the context of microbiomes associated with PsA, psoriasis of the skin (Ps), new-onset rheumatoid arthritis (NORA) and healthy controls, the present inventors determined absolute amounts of microbiota-derived SCFAs and MCFAs for all groups. Results presented herein reveal that quantities of fecal SCFAs—including Acetate, Butyrate and Propionate—were similar in all three groups. Levels of the MCFAs Hexanoate and Heptanoate were, however, significantly reduced in both PsA and Ps compared to controls (FIG. 1; $P<0.05$, and $P<0.01$, respectively).

Figure 2:
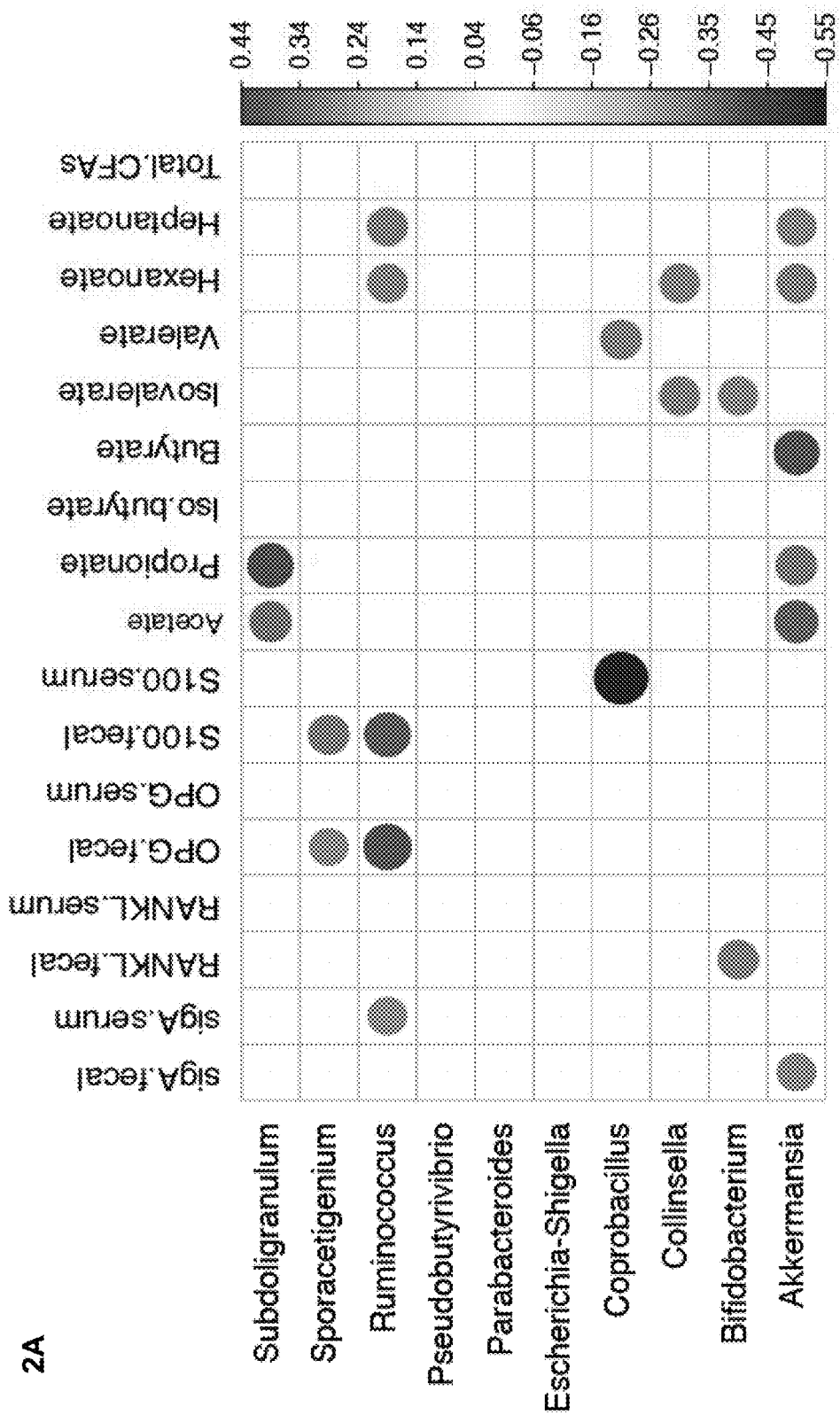
FIGS. 2A and 2B. Correlations between gut microbiota and metadata. Relative abundance of gut microbiota was correlated with levels of various proteins and fatty acids in serum and/or fecal samples. Heatmaps showing correlations between patient metadata and intestinal microbiota at (2A) genus level or (2B) OTU level. Circle sizes and color intensity represent magnitude of correlation. Blue circles=positive correlations; red circles=negative correlations.
Figure 3:
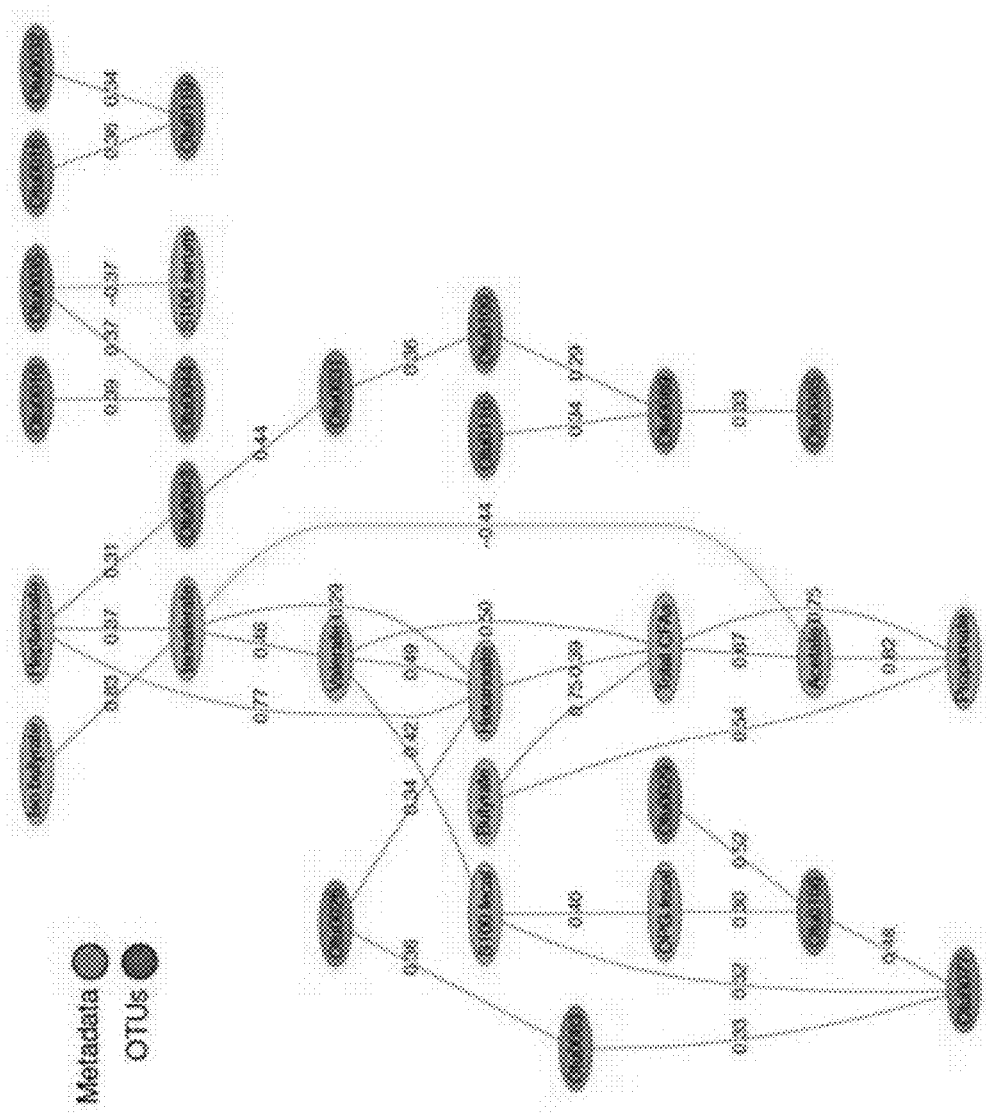
FIG. 3. Optimal Bayesian network analysis.

The present inventors also investigated potential correlations between decreased taxa in Ps and PsA and the various measured fecal and serum proteins and metabolites (FIG. 2). An optimal Bayesian network, which incorporates correlations between taxa, was also performed (FIG. 3). This analysis revealed that, at the genus level, the relative abundance of intestinal *Akkermansia* and *Ruminococcus*—both low in PsA—had a significant positive correlation with Heptanoate and Hexanoate (FIG. 2A). *Akkermansia* (as well as OTU85) was inversely correlated with fecal levels of sIgA and the SCFAs Acetate and Butyrate. At the OTU level (FIG. 2B), OTU43 (*Coprococcus*), diminished in both Ps and PsA, was also positively correlated with quantities of fecal Heptanoate and Hexanoate. This OTU correlated with OTU31, which in turn positively correlated with OTU109 (FIG. 3), all of which were also decreased in both groups of patients. Taken together, these interactions describe a potential distinctive pattern representative of the PsA gut microbiota and its metabolites, characterized by lower relative abundance of several taxa and decreased levels of fecal MCFAs.

Building on these results and the knowledge that MCFAs and SCFAs are structurally similar, the present inventors developed regimens for treating a subject afflicted with PsA that call for administration of at least one SCFA, at least one MCFA, or a combination of at least one SCFA and at least one MCFA or compositions of any of the aforementioned to the subject afflicted with PsA. With respect to structure, MCFAs are typically defined as comprising 6-12 carbon fatty acid esters of glycerol and SCFAs have up to five carbon fatty acid esters of glycerol atoms. Long chain fatty acids are typically defined as having more than twelve carbon atoms per molecule. MCFAs and SCFAs are readily absorbed by the skin and penetrate the skin at a substantially higher rate than that of long chain fatty acids. Short- and medium-chain fatty acids are also absorbed directly into the blood via capillaries lining the intestine and are transported through the portal vein like other absorbed nutrients. MCFAs are relatively uncommon in nature, but are found at significant levels in some plants and substances derived therefrom. See also U.S. Pat. No. 5,175,190; Jiang et al. (2013, Peptides 50:129-138); and Van Immerseel et al. (2006, Avian Pathol 35:182-188), the entire content of each of which is incorporated herein by reference.

By way of background, the role of SCFAs has been studied in a variety of inflammatory and immune responses and diseases, including IBD and obesity. SCFAs are known to act via two principal mechanisms: a) by signaling through G-protein coupled receptors (GPCRs) such as GPR43 (also known as FFAR2), GPR41 and GPR109A; and b) by inhibiting histone deacetylases (HDACs), thereby permitting gene transcription. The mechanistic effects of MCFAs, however, remain insufficiently studied. However, catabolic steps for their production by gut microbiota, enzymatic pathways, and absorption routes, as well as downstream biochemical degradation are identical to those utilized by SCFAs. See, for example, Marks' Basic Medical Biochemistry: A Clinical Approach (A. Peet, 2013; Fourth Edition; Lippincott Williams & Wilkins); You et al. (PEN J Parenter Enteral Nutr. 2008; 32(2): 169-175); and Jensen et al. (1994, Ann Nutr Metab 38:104-116). Accordingly, the surprising results presented herein in combination with the above-described parallels noted between MCFAs and SCFAs led the present inventors to reason that both SCFAs and MCFAs could be utilized interchangeably for experimental and mechanistic approaches in animal models of psoriatic disease.

In accordance with these discoveries, methods for treating PsA are presented herein that comprise administering to a subject afflicted with PsA a therapeutically effective amount of at least one MCFA or a composition thereof, at least one SCFA or a composition thereof, or a combination of at least one MCFA and at least one SCFA or a composition thereof, wherein administering the therapeutically effective amount of the at least one MCFA or a composition thereof, the at least one SCFA or a composition thereof, or the combination of the at least one MCFA and the at least one SCFA or a composition thereof treats the subject afflicted with PsA. Also encompassed herein is at least one MCFA or a composition thereof, at least one SCFA or a composition thereof, or a combination of at least one MCFA and at least one SCFA or a composition thereof for use in the treatment of PsA in a subject in need thereof. Use of at least one MCFA or a composition thereof, at least one SCFA or a composition thereof, or a combination of at least one MCFA and at least one SCFA or a composition thereof in the preparation of a medicament for the treatment of PsA is also envisioned herein. MCFAs are known in the art and described in, for example, FIGS. 1 and 2.

Exemplary MCFAs described herein include Heptanoate and Hexanoate. SCFAs are also known in the art and described in, for example, Smith et al. (2013, Science 341:569-573); Maslowski et al. (2009, Nature 461:1282-1286); Huang et al. (2011, Arch Oral Biol 56:650-654), the entire content of each of which is incorporated herein by reference. Exemplary SCFAs described herein include acetic acid ($CH_3COOH$), butyric acid ($CH_3(CH_2)_2COOH$), iso-butyric acid (($CH_3)_2CHCOOH$), propionic acid ($CH_3CH_2COOH$), valeric acid ($CH_3(CH_2)_3COOH$), and iso-valeric acid (($CH_3)_2CH\ CH_2COOH$); the corresponding salts for which are acetate, butyrate, iso-butyrate, propionate, valerate, and iso-valerate, respectively.

Hexanoates are salts of Hexanoic acid (caproic acid), which is the carboxylic acid derived from hexane with the general formula of $C_5H_{11}COOH$. Information pertaining to various hexanoates is publicly available and hexanoates can be purchased from a variety of suppliers. Information regarding sodium Hexanoate, an exemplary Hexanoate, is, for example, available via ChemSpider ID: 23257. The molecular formula is $C_6H_{11}NaO_2$. Sodium Hexanoate is, for example, available for purchase from ABI Chemicals, Santa Cruz Biotechnology, and Sigma-Aldrich. Methods for making sodium Hexanoate are also known in the art.

Information pertaining to various heptanoates is publicly available and heptanoates can be purchased from a variety of suppliers. Information regarding Heptanoate, is, for example, available via ChemSpider ID: 84004. Heptanoate has a general formula of $C_7H_{13}O_2$.

Other MCFAs include octanoic acid (caprylic acid; $CH_3(CH_2)_6COOH$), the salt of which is referred to as octanoate; decanoic acid (capric acid; $CH_3(CH_2)_8COOH$), the salt of which is referred to as decanoate; and dodecanoic acid (lauric acid; $CH_3(CH_2)_{10}COOH$), the salt of which is referred to as dodecanoate. Derivatives of various MCFAs are also known and envisioned for use in methods described herein. Such derivatives include geranic acid, a derivative of octanoic acid, the formula for which is 3,5-dimethyl, 2,6-octadienoic acid. Derivatives of geranic acid are also envisioned, including 3,7-dimethyl, 6,7-dihydroxyoct-2-enoic acid (MHA). See, for example, U.S. Pat. No. 5,175,190, the entire content of which is incorporated herein by reference, which describes these derivatives and synthesis thereof.

Additional information relating to MCFAs and derivatives thereof is presented in Jiang et al. (2013, Peptides 50:129-138), wherein structures for a variety of various fatty acids and derivatives thereof and commercial vendors from which these fatty acids and derivatives thereof can be purchased are described. Additional information pertaining to SCFAs and MCFAs and commercial availability thereof is also detailed in, for example, Huang et al. (2011, Arch Oral Biol 56:650-654), the entire content of which is incorporated herein by reference. More particularly, Huang et al. (2011, Arch Oral Biol 56:650-654) indicates that a variety of SCFAs and MCFAs are available from Cayman Chemicals (Ann Arbor, Mich.) or Sigma (St. Louis, Mo.).

In a further aspect, diagnostic biomarkers/indicators described herein are also envisioned as therapeutic biomarkers/indicators. In that determining the presence and/or amount of one of the aforementioned biomarkers/indicators (e.g., a by-product of a bacterial genus or species that is underrepresented in PsA) can be used for diagnosing PsA and/or predicting the likelihood that a subject will be afflicted with PsA, it is envisioned that determining the presence and/or amount of one of these biomarkers/indicators can also be used as a therapeutic indicator. It is to be understood that in such therapeutic embodiments, detection of the relevant biomarkers/indicators is performed before and after administration of the potential therapeutic compound for the purposes of comparison.

In a particular embodiment, detection of the presence of or an increase in a by-product of a bacteria of at least one of the following bacterial genera: *Akkermansia, Ruminococcus, Pseudobutyrivibrio, Coprococcus, Coprobacillus*, Unclassified (UC)_*Clostridia, Verrucomicrobiae, Verrucomicrobia*, and *Verrucomicrobiales* or a particular species thereof, such as *R. gnavus*, following treatment with a potential therapeutic compound (e.g., a biotic supplement such as a composition described herein or a fecal sample) would indicate that the therapeutic compound is efficacious. Under such a circumstance, the presence of or an increase in a by-product of a species of the *Coprococcus* genera, for example, following treatment as compared relative to the low or negligible levels of by-products of these species prior to treatment indicates that the compound is efficacious.

In another particular embodiment, detection of no change or a further decrease in the levels of a by-product of a bacteria of at least one of the following bacterial genera: *Akkermansia, Ruminococcus, Pseudobutyrivibrio, Coprococcus, Coprobacillus*, Unclassified (UC)_*Clostridia, Verrucomicrobiae, Verrucomicrobia*, and *Verrucomicrobiales* or a particular species thereof, such as *R. gnavus*, following treatment with a potential therapeutic compound would indicate that the therapeutic compound is not efficacious. Under such a circumstance, the absence of a change in levels of or an even further decrease in a by-product of a species of the *Coprococcus* genera, for example, following treatment as compared relative to the low or negligible levels of a by-product of these species prior to treatment indicates that the compound is not efficacious.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [RI. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The subject or patient is preferably an animal, including but not limited to animals such as mice, rats, cows, pigs, horses, chickens, cats, dogs, etc., and is preferably a mammal, more preferably a primate, and most preferably a human.

In a particular embodiment, the animal is of an animal model species, for example, a mouse animal model system of PsA. Such animal models are known in the art and described in, for example, Weitz et al. (Curr Rheumatol Rep. 2013 November; 15(11):377; the entire content of which is incorporated herein by reference).

The term "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term "prophylaxis" is related to "prevention" and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term psoriatic arthritis of PsA refers to those individuals meeting three or more points from the ClASsification of Psoriatic ARthritis (CASPAR) criteria, including: (1) the presence of psoriasis (current, history of, or family history of), (2) psoriatic nail dystrophy, (3) a negative rheumatoid factor (RF) test result, (4) dactylitis (history of or current), and (5) radiographic evidence of juxta-articular new bone formation.

As used herein, the term psoriasis or Ps refers to patches of thick, inflamed skin covered with silvery scales. These patches, or plaques, are usually itchy. They most often occur on the elbows, knees, other parts of the legs, scalp, lower back, face, palms, and soles of the feet, but they can occur on skin anywhere on the body. The disease may also affect the fingernails, the toenails, and the soft tissues of the genitals, and inside the mouth.

As used herein, the term arthritic symptoms refers to joint swelling, tenderness, redness, warmth or a combination thereof.

As used herein, the term "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, regulatory or suppressor T cells, and/or cytotoxic T cells directed specifically to an antigen or antigens included in the composition or vaccine of interest.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to preferably reduce by at least about 30 percent, more preferably by at least 50 percent, most preferably by at least 90 percent, a clinically significant change in a pathological feature of a disease or condition.

The present invention also provides pharmaceutical compositions. Such compositions comprise a therapeutically effective amount of an agent and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions will contain a therapeutically effective amount of the compound, preferably in purified form, together with a suitable amount of carrier so as to provide the form for proper administration to the subject. The formulation should suit the mode of administration.

Compositions containing molecules or compounds described herein can be administered for diagnostic and/or therapeutic treatments. In therapeutic applications, compositions are administered to a patient already suffering from PsA in an amount sufficient to at least partially arrest the symptoms of the disease and its complications. An amount adequate to accomplish this is defined as a "therapeutically effective amount or dose." Amounts effective for this use will depend on the severity of the disease and the weight and general state of the patient.

With regard to oral SCFA dosing, exemplary dosing parameters are presented in the Examples set forth herein and described in Smith et al. (2013, Science 341:569-573); Maslowski et al. (2009, Nature 461:1282-1286); and Huang et al. (2011, Arch Oral Biol 56:650-654), the entire content of each of which is incorporated herein by reference. For mice, sodium acetate (67.5 mM), sodium propionate (25.9 mM), and sodium butyrate (40 mM) dissolved in water and administered ad libitum provides a therapeutically effective dose for treating PsA in the animal model of PsA described herein. Efficient oral uptake of SCFAs in mice is observed in a dose range of up to 200 nM (Smith et al. 2013, Science 341:569-573). Scaling up for larger mammals, such as, for example, humans can be approached in accordance with standard practice based on body mass.

With regard to oral MCFA dosing, exemplary dosing parameters are presented in the Examples set forth herein and described in Huang et al. (2011, Arch Oral Biol 56:650-654) and Carlson et al. (2015, Metabolism Clinical and Experimental 64:274-282) and references cited therein, the entire content of each of which is incorporated herein by reference. For mice, food supplemented with medium chain triglycerides (MCTs) and administered ad libitum is envisioned to provide a therapeutically effective dose for treating PsA in the animal model of PsA described herein. Scaling up for larger mammals, such as, for example, humans can be approached in accordance with standard practice based on body mass.

With regard to rectal or anal administration of SCFAs and/or MCFAs, delivery of SCFAs and/or MCFAs or compositions thereof may be achieved via suppository, enema (using, for example, a rectal bulb syringe), and/or a specialized catheter designed for rectal administration of medications and/or liquids. In general, an active agent that is administered rectally typically has faster onset, higher bioavailability, shorter peak, and shorter duration than the same active agent administered via the oral route. In that the rectal route bypasses about two-thirds of the first-pass metabolism because the rectum's venous drainage is two-thirds systemic (middle and inferior rectal vein) and one-third portal (superior rectal vein), active agents delivered thereby can reach the circulatory system in greater concentrations and with fewer alterations than when delivered via an oral route. See, for example, de Boer et al. (1982, Clin Pharmacokinet 7:285-311) and van Hoogdalem et al. (1991, Clin Pharmacokinet 21:11-26). Dosing parameters for oral and rectal administration of active agents are typically similar or identical, but may require optimization depending on the active agent. See, for example, Scolnik et al. (2002, Pediatrics 110:553-556) and Wilkinson et al. (1992, Cancer Chemothera Pharmacol 31:251-254). For some active agents, however, rectal delivery and absorption have been shown to reduce the dose required to achieve therapeutic effect.

Also encompassed herein are therapeutic compositions useful for practicing the therapeutic methods described herein. A subject therapeutic composition may include, in admixture, a sterile manmade pharmaceutically acceptable or physiologically compatible excipient (carrier) and one or more of an agent as an active ingredient (e.g., a byproduct of a bacterial genera or species, such as a SCFA and/or a MCFA or a combination of SCFAs and MCFAs), which promotes normalization or restoration of normal immune response in the gut and systemically so as to reduce inflammatory immune responses, as described herein as an active ingredient. In a particular embodiment thereof, the therapeutic compositions described herein do not comprise long chain fatty acids.

The preparation of therapeutic compositions which contain active ingredients, such as the MCFAs and SCFAs described herein, is well understood in the art. Such compositions may be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. As described herein above, suitable excipients are, for example, water, saline, dextrose, glycerol, ethanol, or the like and combinations thereof.

A MCFA or SCFA can be formulated into the therapeutic composition as neutralized pharmaceutically acceptable salt forms. Pharmaceutically acceptable salts include the acid addition salts (formed with the free amino groups of, e.g., a polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The MCFA- and/or SCFA-containing compositions may be administered orally or anally per unit dose. The term "unit dose" when used in reference to a therapeutic composition described herein refers to physically discrete units suitable as unitary dosage for humans, each unit containing a predetermined quantity of active material calculated to produce the desired therapeutic effect in association with the required diluent; i.e., carrier, or vehicle. To achieve systemic dosing, the MCFA- and/or SCFA-containing compositions described herein are not administered topically.

The MCFA- and/or SCFA-containing compositions may be conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimens for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

As used herein, the term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. In a particular embodiment, the isolated nucleic acid sequence is a cDNA.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program and are known in the art.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence. When referring to a composition consisting essentially of a SCFA or a MCFA, for example, the composition may consist essentially of the SCFA or MCFA, thereby indicating that the SCFA or a MCFA in the composition is present in the absence of other SCFAs or MCFAs. Under circumstances wherein a composition consists essentially of at least one SCFA, at least one MCFA, or a combination of at least one SCFA and at least one MCFA, the composition consists of only those SCFAs and/or MCFAs specifically indicated in essentially pure, isolated form and a pharmaceutically acceptable carrier.

A "replicon" is any genetic element, for example, a plasmid, cosmid, bacmid, phage or virus that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence, which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to a primer and a probe as described herein and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers and/or probes may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

In a particular embodiment, oligonucleotides that hybridize to nucleic acid sequences identified as specific for, for example, any one of a bacterial genera or species underrepresented in PsA as described herein, are at least about 10 nucleotides in length, more preferably at least 15 nucleotides in length, more preferably at least about 20 nucleotides in length. Further to the above, fragments of nucleic acid sequences identified as specific for a bacterial genera or species underrepresented in PsA described herein represent aspects of the present invention. Such fragments and oligonucleotides specific for same may be used as primers or probes to determining the amount of a bacterial genera or species underrepresented in PsA in a biological sample obtained from a subject. Primers such as those described herein, which bind specifically to a bacterial genera or species underrepresented in PsA may, moreover, be used in polymerase chain reaction (PCR) assays in methods directed to determining the amount of a bacterial genera or species underrepresented in PsA in a biological sample obtained from a subject.

By "solid phase support or carrier" is intended any support capable of binding an oligonucleotide, antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present methods and/or compositions. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art are aware of many other suitable carriers for binding oligonucleotide, antibody, or antigen, and are able to ascertain the same by use of routine experimentation.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

Kits

Also encompassed herein is a diagnostic pack or kit comprising one or more containers filled with one or more of the diagnostic reagents described herein. Such diagnostic reagents include fragments and oligonucleotides useful in the detection of a bacterial genera or species underrepresented in PsA in a subject or sample isolated therefrom. Diagnostic reagents may comprise a moiety that facilitates detection and/or visualization. Diagnostic reagents may be supplied in solution or immobilized onto a solid phase support. Optionally associated with such container(s) are buffers for performing assays using the diagnostic reagents described herein, negative and positive controls for such assays, and instructional manuals for performing assays.

Unless defined otherwise, all technical and scientific terms used herein have the same meaning as commonly understood by one of ordinary skill in the art to which this invention belongs.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

All publications mentioned herein are incorporated herein by reference to disclose and describe the methods and/or materials in connection with which the publications are cited.

Example I

Materials and Methods

Study Participants.

Consecutive patients from rheumatology clinics and practice offices of New York University School of Medicine were screened for the presence of PsA [samples and sequences obtained from previously described cohort (12)] or psoriasis of the skin (Ps). After informed consent was signed, each patient's medical history and medications were determined. A screening musculoskeletal examination, laboratory and radiographic assessments were also performed or reviewed. All PsA/Ps patients who met study criteria were offered enrollment. Non-arthritic healthy subjects were also identified from a recently published study (12) and enrolled as controls.

This study was approved by the Institutional Review Board of NYU School of Medicine, and written informed consent was obtained from all study participants.

Inclusion and Exclusion Criteria.

Patients were included as recent-onset PsA if they met Classification Criteria for Psoriatic Arthritis (CASPAR) including presence of current active psoriasis of the skin (Ps) and arthritis, and had never been treated with systemic disease-modifying anti-rheumatic drugs (DMARDs; oral and/or biologic agents) or steroids. Patients were included as Ps without PsA if they were diagnosed by a dermatologist and had no arthritis, enthesitis or dactylitis (as assessed by a rheumatologist) at enrollment. Healthy controls were age-, sex-, and ethnicity-matched individuals with no personal history of psoriasis, autoimmune disease (including IBD) or inflammatory arthritis. Criteria for inclusion required that all subjects be age 18 years or older.

Exclusion criteria applied to all groups were as follows: recent (<3 months prior) use of any antibiotic therapy, current extreme diet (e.g., parenteral nutrition or macrobiotic diet), known history of malignancy or IBD, current consumption of probiotics, or any gastrointestinal tract surgery leaving permanent residua (e.g., gastrectomy, bariatric surgery, or colectomy).

Sample Collection and DNA Extraction.

Fecal samples were obtained for all participants within 24 hours of production. DNA extraction, amplification of the V1-V2 16S rRNA gene region and 454 pyrosequencing were performed for all samples as recently published (13).

Sequence Analysis.

Sequencing data was compiled and processed using mothur software and converted to standard Fasta format as described in prior studies (13). Briefly, sequences were grouped into operational taxonomic units (OTUs) using the average neighbor algorithm. Sequences with a distance-based similarity of ≥97% were assigned to the same OTU. For each sample, microbial diversity was estimated by calculating the Shannon diversity index or Faith's phylodiversity index. Phylogenetic classification was performed using the Bayesian classifier algorithm, with a boot-strap cutoff value of 60%. For microbiota comparison between samples, only 2718 sequences (number of high-quality sequences obtained from the sample with lowest counts) were used for all data analyses.

For UniFrac analysis, a phylogenetic tree was inferred using clearcut (14), on the 16S rRNA sequence alignment generated by mothur. Unweighted UniFrac was run using the resulting tree. Principal Coordinate of Analysis (PCoA) was performed on the resulting matrix of distances between each pair of samples.

Serum and Fecal Measurement of sIgA, Proteins and Cytokines.

Protein concentration in feces was measured by the BCA method. ELISA assays were performed to determine serum and fecal concentrations of secretory IgA (sIgA; Immundiagnostik AG), receptor activator of nuclear factor kappa-B ligand (RANKL, Immundiagnostik AG), osteoprotegerin (OPG; Raybio), S-100A12 protein (S100, Circulex) utilizing a validated protocol (15).

Human Leukocyte Antigen (HLA) Allele Determination.

Genomic DNA was isolated from peripheral blood of PsA patients using QIAamp Blood Mini Kit (Qiagen). HLA-B and C alleles were determined by Single Specific Primer-Polymerase Chain Reaction (SSP-PCR) methodologies (Weatherall Institute for Molecular Medicine, Oxford, UK) (12).

Fecal Measurement of Fatty Acids (FAs).

Levels of fecal short-chain fatty acids (SCFAs) and medium-chain fatty acids (MCFAs) were measured by gas chromatography-mass spectrometry (GC-MS) at the University of Michigan Metabolomics Core. Samples were extracted by aqueous extraction solvent, homogenized and centrifuged. GC (Agilent 6890) separation was performed using a ZB-Wax plus column (Phenomenex). A single quadrupole mass spectrometer (Agilent, 5973 inert MSD) was used to identify and quantitate the SCFAs, using Agilent Chemstation software. The acquired GC-MS data were processed by Agilent mass hunter quantitative analysis software (version B.06). Retention times and characteristic masses of FAs were used for peak identification and quantification. Absolute quantities of FAs were normalized to the sample mass.

Statistical Analysis.

In order to identify differentially abundant bacterial taxa among groups, the present inventors applied the LefSe analytical method (16). In brief, LefSe [linear discriminant analysis (LDA) coupled with effect size measurements] is a metagenomic biomarker-discovery approach based on an algorithm that first performs a nonparametric Kruskal-Wallis test in order to identify bacterial taxa whose relative abundance is significantly different in a group of interest (e.g., PsA) compared to controls (i.e., healthy or Ps). Subsequently, LefSe applies LDA to those bacterial taxa identified as significantly different (P <0.05) and further assesses the effect size of each differentially abundant taxon (16). Only those taxa that obtain a log LDA score >2 are ultimately considered. As a result, LefSe indicates those taxa and OTUs that better discriminate between phenotypes. In addition, since LefSe does not consider multiple hypothesis testing, the present inventors further applied the non-parametric Wilcoxon test for every taxon at every phylogenetic level whose average abundance was higher than 0.1% (in any of the three groups analyzed). The Benjamini and Hochberg false discovery rate test (FDR) was then applied. Those bacterial taxa/OTUs with P<0.05 and FDR q value lower than 0.2 were considered as the main bacterial taxa differentiating between groups of samples. For cross-sectional analyses of baseline characteristics and comparison of diversity indexes between groups, differences were evaluated using Student's t-test, Mann-Whitney U test, one-way ANOVA, AMOVA or chi-square test, as appropriate. Two-tailed tests were used for significance testing, and P values less than 0.05 were considered significant.

Correlation and Network Analyses.

Spearman correlation between taxa/OTUs, FAs, sIgA and inflammatory proteins was performed using the statistical R package command cor.test. Correlations were performed only in those taxa/OTUs found to be statistically significant between groups by LefSe. P values under 0.05 were considered significant.

The Optimal Bayesian network structure was inferred through 'high climbing' algorithm implemented in the bnlearn R package (17). Regularized inference was carried out by rejecting those relations between nodes with an associated Spearman correlation p-value greater than 0.05.

Results

Patients.

Only patients with recent-onset, DMARD-naïve PsA were included in the study; 56% were female and mean age was 46.2 years (Table 1). Mean disease duration was 0.8 months and no patient had ever received steroids, oral DMARDs, or biologic drugs. All patients had active skin psoriatic lesions and clinical or radiographic evidence of arthritis at enrollment (25% presented with axial arthritis). Ps and healthy controls were age-, sex-, and ethnicity-matched to PsA subjects. Baseline characteristics are described in Table 1.

TABLE 1

Demographic and clinical data among patients with recent-onset psoriatic arthritis (PsA), psoriasis of the skin (Ps) and healthy control participants.

| Characteristic | PsA (n = 16) | Ps (n = 15) | Healthy Controls (n = 17) |
|---|---|---|---|
| Age, years, mean (median) | 46.2 (40) | 39.4 (37) | 42.2 (39) |
| Female, % | 56% | 53% | 64% |
| Ethnicity, white * | 62% | 66% | 59% |
| HLA-B27, % | 12% | n/a | n/a |
| HLA-Cw6, % | 18% | n/a | n/a |
| HLA-B27 and/or Cw6, % | 30% | n/a | n/a |
| Disease duration, months, mean (median) | 0.8 (0) | 16 (11) | n/a |
| Disease activity parameters (articular) | | | |
| CRP, mg/l, mean (median) | 7.5 (0) | 1 (0) | 0 |
| DAS28, mean (median) | 4.8 (4.7) | n/a | n/a |
| Patient VAS pain, mm, mean (median) | 50.6 (45) | n/a | n/a |
| Active Joint Count, mean (median) | 4.7 (3) | n/a | n/a |
| Axial involvement, % | 25% | n/a | n/a |
| Disease activity parameters (skin) | | | |
| PASI, mean (median) | 5.2 (3.8) | 6.3 (4.3) | n/a |
| Nail Psoriasis, % | 75% | 69% | n/a |
| Medication use | | | |
| NSAIDs, current % | 75% | 0% | n/a |
| Methotrexate, % | 6%** | 0% | n/a |
| Prednisone, % | 0% | 0% | n/a |
| Biological agent, % | 0% | 0% | n/a |

Abbreviations: PsA, psoriatic arthritis; Ps, psoriasis of the skin only; CRP, C-reactive protein; DAS28, Disease Activity Score with 28 joint count; VAS, visual analog scale; PASI, Psoriasis Area and Severity Index; NSAIDs, non-steroidal anti-inflammatory drugs.
* Including Hispanic whites.
**One patient had received one dose of methotrexate the week prior to enrollment.

MCFAs, but not SCFAs, are Decreased in Both PsA and Ps Fecal Samples.

Since microbiota-derived SCFAs and MCFAs have been implicated in intestinal health, the present inventors determined absolute amounts of these metabolites in all groups. Quantities of fecal SCFAs—including Acetate, Butyrate and Propionate—were similar in all three groups. Interestingly, however, levels of the MCFAs Hexanoate and Heptanoate were significantly reduced in both PsA and Ps compared to controls (FIG. 1; P<0.05, and P<0.01, respectively).

Characteristic Interrelations of Gut Microbiota and Metadata in PsA.

Because of univariate associations between groups, gut microbiota and metadata, the present inventors set out to describe correlations between decreased taxa in Ps and PsA and the various measured fecal and serum proteins and metabolites (FIG. 2). An optimal Bayesian network, which incorporates correlations between taxa, was also performed (FIG. 3). This analysis revealed that, at the genus level, the relative abundance of intestinal *Akkermansia* and *Ruminococcus*—both low in PsA—had a significant positive correlation with Heptanoate and Hexanoate (FIG. 2A). *Akkermansia* (as well as OTU85) was inversely correlated with fecal levels of sIgA and the SCFAs Acetate and Butyrate. Interestingly, *Coprobacillus*, a genus decreased in Ps, negatively correlated with S100 levels in serum. At the OTU level (FIG. 2B), OTU43 (*Coprococcus*), diminished in both Ps and PsA, was also positively correlated with quantities of fecal Heptanoate and Hexanoate. This OTU correlated with OTU31, which in turn positively correlated with OTU109 (FIG. 3), all of which were also decreased in both groups of patients. OTU16 (UC_Lachnospiraceae), low in PsA, was the only OTU positively correlated with fecal levels of RANKL (also decreased in PsA), and co-occurred with two other OTUs that were relatively decreased in PsA: OTU32 and OTU119 (FIG. 3). Taken together, these interactions describe a potential distinctive pattern representative of the PsA gut microbiota and its metabolites, characterized by lower relative abundance of several taxa and decreased levels of fecal RANKL and MCFAs.

Finally, the Bayesian network analysis showed that OTUs 10 (*Parabacteroides*), 44 and 35 (both UC_Lachnospiraceae) also clustered together (FIG. 3), with the latter taxa revealing the highest inverse correlation with serum levels of S100 (FIG. 2B). These interactions differentiate the gut microbiota of the Ps cohort and its associations with systemic inflammatory markers.

Discussion

An expanding body of literature has linked the intestinal microbiota, gut inflammation (both clinical and subclinical), and the different phenotypic expressions of spondyloarthritis.

Two decades ago, seminal work determined the role of gut microbiota in the development of arthritis and colitis in HLA-B27 transgenic rats (7). Since then, many studies have contributed to strengthen this hypothesis, namely that in genetically susceptible subjects a state of gut microbial dysbiosis (alteration in the homeostasis of bacterial composition) promotes an exaggerated immune response in the host's intestinal lamina propria, activating systemic inflammation and ultimately leading to joint disease. The role of HLA-B27 and related genes was recently validated in AS, IBD and PsA (19). Subclinical histological and molecular markers of gut inflammation are also found in patients with AS (20,21) and with PsA (10). While these studies addressed the activation of host mucosal immunity, they did not directly examine the role of the intestinal microbiome. The link between intestinal bacteria and SpA has been investigated separately. Prior studies, however, utilized indirect serologic methods, classic culture approaches and/or limited, low-throughput PCR/DGGE-based techniques (22), assessing for prevalence of only a handful of taxa.

Utilizing high-throughput, culture-independent, 16S rRNA gene pyrosequencing technology the present inventors have shown, for the first time, that patients with PsA and Ps have a decreased diversity in their gut microbiota, mainly due to lower relative abundance of several taxa. Some of this taxa reduction is shared between both conditions [i.e. OTU 43 (*Coprococcus*)], suggesting a distinctive intestinal gut microbiota that is common in psoriasis of the skin but independent of arthritis. Interestingly, however, other genera such as *Ruminoccocus* and *Akkermansia* are uniquely decreased in PsA.

This is intriguing for several reasons. First, similar results have been consistently reported (and replicated) in microbiome studies of patients with IBD, and particularly in those with Crohn's disease (23). Second—and perhaps more remarkable—is the present finding that this relatively lower diversity in PsA and IBD microbiota is mainly driven by a decrease in phylogenetically similar microbiome members. Several reports showed that *Akkermansia* and *Ruminococcus* species, as well as *Alistipes* genus, are also diminished in IBD patients. *Akkermansia* is detectable in the majority of healthy subjects (24) and is an important component in two of three recently described human gut enterotypes (25). Using publicly available genetic alignment tools (BLAST), the present inventors found that OTU85 has 100% sequence identity to *Akkermansia muciniphila* and is virtually absent from our PsA cohort.

Functionally, *A. muciniphila* is predominantly a mucus-degrading gut symbiont that converts mucin into short-chain fatty acids (SCFAs) Acetate and Propionate, activating host epithelial cells and stimulating an adequate immune response. Notably, *A. muciniphila* was the most abundantly identified mucolytic mucosa-associated bacterium in healthy controls vs IBD patients (26-28), suggesting a protective role for this taxon. In two recent studies, Ruminococcaceae were also underrepresented in gut microbiota from IBD patients, particularly in ileal Crohn's disease (29,30). Many *Ruminococcus* species, except *R. gnavus*, are decreased in Crohn's disease (31). Interestingly, several *Ruminococcus* species are also mucin-degrading bacteria and important in maintaining gut homeostasis, particularly via the production of SCFAs. SCFAs in turn promote intestinal health, creating favorable conditions for resistance to pathogenic bacteria and protection against colitis (32). None of the SCFAs analyzed in our cohort, however, were significantly lower in PsA patients.

Other gut bacterial genera were relatively decreased in our PsA cohort, including OTU43 (*Coprococcus*). Although not described as underrepresented in IBD, our network algorithm did reveal that its reduced presence in PsA is directly correlated with significantly lower levels of Hexanoate and Heptanoate (same effect observed for OTU85). Although insufficiently studied, two reports have shown a decrease of these MCFAs in IBD patients (33,34). Interestingly, MCFAs display antibacterial effects and were shown to activate peroxisome proliferator activated receptor (PPAR)-γ (35), which in turn is known to ameliorate colitis in animal models (36) and human Crohn's (37).

Example II

Materials and Methods

Animal Model: To generate the animal model of PsA driven by Th17 inflammation, a hyperactive mutant of STAT3, STAT3C, was inserted into the ROSA26 locus. To express STAT3C specifically in T lymphocytes, the present inventors took advantage of a T cell-specific Cre line, CD4Cre. By 6 weeks of age, most animals develop striking skin inflammation reminiscent of psoriasis and secondary to Th17 infiltration of the skin. Histology of the skin from CD4Cre STAT3Cs$^{topfl/fl}$ mice reveals striking acanthosis, parakeratosis, hyperkeratosis and occasional Munro's abscesses. By 6-8 wks of age, mice develop kephosis and marked bone mineral density loss as judged by DEXA scans and micro CT evaluation of the long bones and spine. Joint space is also impacted by Th17 driven inflammation as is evident from micro-CT analysis of the paws.

SCFA supplementation: Mice were allowed to drink ad libitum. SCFA supplementation was achieved by dissolving sodium acetate, sodium propionate, and sodium butyrate (Sigma-Aldrich s2889-250 g; p1880-500 g; 303410-100 g) at concentrations of 67.5 mM, 25.9 mM and 40 mM, respectively. Water was changed weekly and administered from birth.

Results

Figure 4:
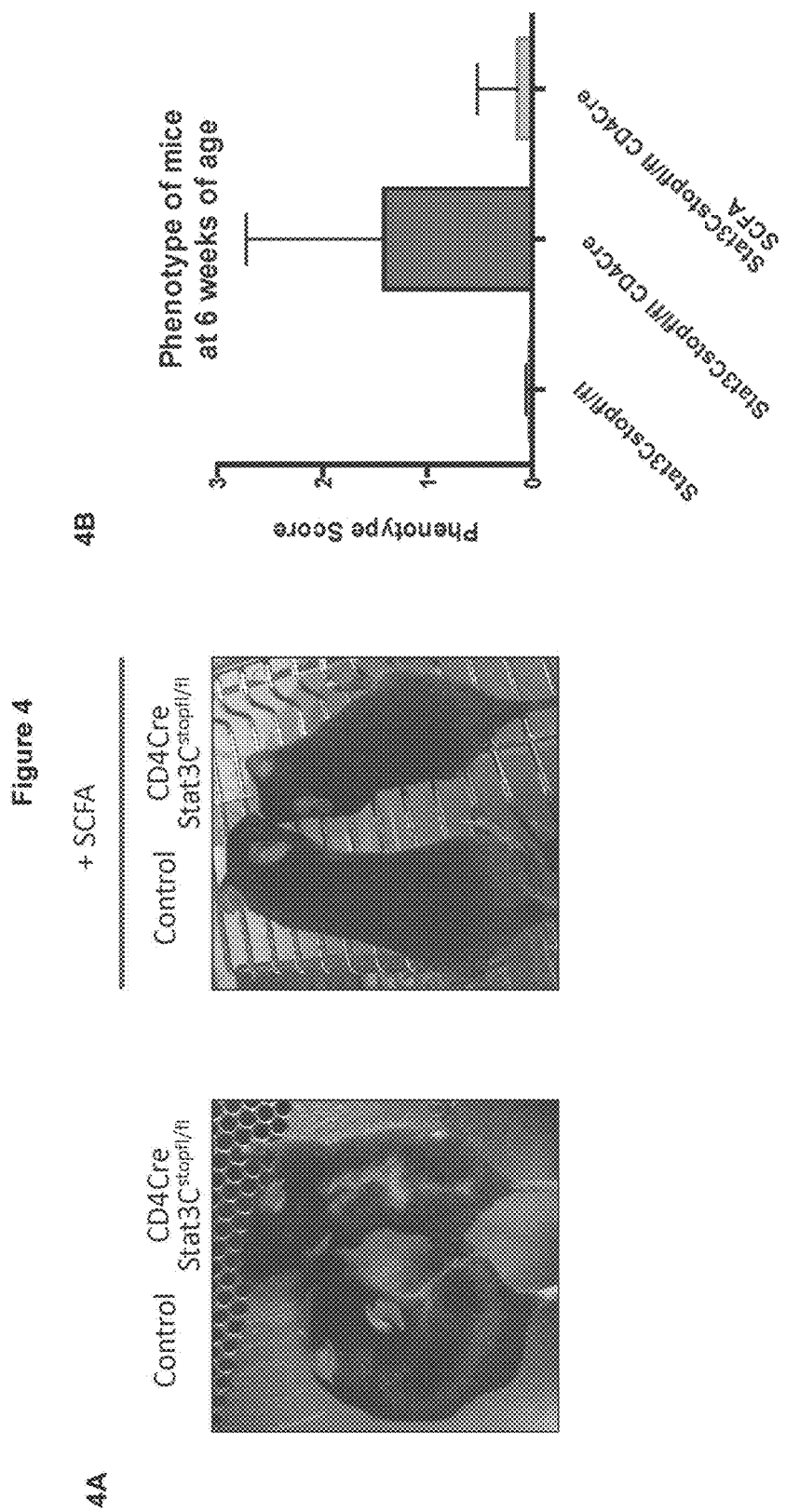
FIGS. 4A and 4B. SCFA supplementation ameliorates the disease in a mouse model of PsA: (4A) Representative image of 6 week old CD4Cre STAT3$0^{stopfl/fl}$ animals and littermate controls with and without SCFA supplementation. (4B) Rheumatic disease score average for animals either provided with SCFA supplement or in control cages. CD4Cre STAT3C$^{stopfl/fl}$ animals and littermate controls were given water supplemented with SCFAs from birth ad libitum. Water was changed once a week. Phenotype of the animals was scored based on the following criteria: 0—no irritation and no spinal deformity; 1—thinning fur or dry tail/ears; 2—obvious fur loss; 3—greater than 50% hair loss and/or very dry crusty skin; an additional point was added for animals that exhibited obvious kephosis.

As shown in FIG. 4A, SCFA supplementation ameliorates the disease in a mouse model of PsA as reflected, for example, by restoration of normal fur continuity and luster in animals provided access to SCFA supplement. As made evident by FIG. 4B, SCFA supplementation also ameliorates symptoms indicative of rheumatic disease as reflected by the essentially normal score average for animals provided with SCFA supplement.

Experiments are ongoing to assess the effect of MCFA supplementation on the aforementioned animal model of PsA driven by Th17 inflammation, namely CD4Cre STAT3Cs$^{topfl/fl}$ mice.

MCFA supplementation: Control and MCFA supplemented food was purchased from DYETS (Bethlehem, Pa.). MCFA supplemented food: Catalog #180977 supplemented with medium chain triglycerides (MCT) oil (MCT Gold; Ultimate Nutrition; available for purchase from Amazon). The MCFA supplemented food was generated in accordance with Carlson et al. (2015, Metabolism Clinical and Experimental 64:274-282). See also Reeves et al. (1993, J Nutr 123:1939-1951. Control food: Catalog #180955 control diet supplemented with 10% soybean oil. Food was gamma irradiated and vacuumed packed prior to shipment from DYETS.

Similar diets can be purchased from other purveyors, including Gordon's Specialty Stock Feeds (Yanderra, NSW, Australia) and Research Diets Services (Wijk bij Duurstede, The Netherlands). Alternatively, specialized diets supplemented with MCTs/MCFAs can also be prepared in house.

Breeding cages are supplied with one of the two diets and animals are weaned onto the appropriate diet. The phenotype of the mice will be evaluated twice per week by visual inspection, weight measurement, and eventually fluorescence activated sorting (FACS) analysis of relevant tissues (including skin, gut, bone marrow, and lymph nodes), histological assessment of tissue and tissue sections (of skin and bone) and micro-CT of the long bones and skeleton, once the mice reach 6-8 weeks of age.

Compositional information pertaining to the control and MCSF supplemented diets is presented below:

| DYET# 180955 Modified AIN-93M Purified Rodent Diet with 10% Soybean Oil (w/w) | | | |
| --- | --- | --- | --- |
| Ingredient | kcal./gm | grams/kg | kcal./kg |
| Casein | 3.58 | 140 | 501.2 |
| L-Cystine | 4 | 1.8 | 7.2 |
| Sucrose | 4 | 100 | 400 |
| Cornstarch | 3.6 | 405.68 | 1460.4480 |
| Dyetrose | 3.8 | 155 | 589 |
| Soybean Oil | 9 | 100 | 900 |
| t-Butylhydroquinone | 0 | 0.02 | 0 |
| Cellulose | 0 | 50 | 0 |
| Mineral Mix #210050 | 0.84 | 35 | 29.4 |
| Vitamin Mix # 310025 | 3.87 | 10 | 38.7 |
| Choline Bitartrate | 0 | 2.5 | 0 |
| | | 1000.00 | 3925.9480 |

*Journal of Nutrition* v123, 1943-44(1993)

| DYET# 180977 Modified AIN-93M Purified Rodent Diet with 10.84% Medium Chain Triglycerides (w/w) | | | |
| --- | --- | --- | --- |
| Ingredient | kcal./gm | grams/kg | kcal./kg |
| Casein | 3.58 | 140 | 501.2 |
| L-Cystine | 4 | 1.8 | 7.2 |
| Sucrose | 4 | 100 | 400 |
| Cornstarch | 3.6 | 405.68 | 1460.4480 |
| Dyetrose | 3.8 | 155 | 589 |
| Medium Chain Triglycerides | 8.3 | 108.4 | 900 |

-continued

DYET# 180977
Modified AIN-93M Purified Rodent Diet with
10.84% Medium Chain Triglycerides (w/w)

| Ingredient | kcal./gm | grams/kg | kcal./kg |
|---|---|---|---|
| t-Butylhydroquinone | 0 | 0.02 | 0 |
| Cellulose | 0 | 41.6 | 0 |
| Mineral Mix #210050 | 0.84 | 35 | 29.4 |
| Vitamin Mix # 310025 | 3.87 | 10 | 38.7 |
| Choline Bitartrate | 0 | 2.5 | 0 |
|  |  | 1000.00 | 3925.6680 |

*Journal of Nutrition* v123, 1943-44(1993)

REFERENCES

1. Eder L, Chandran V, Pellet F, Shanmugarajah S, Rosen C F, Bull S B, et al. Human leucocyte antigen risk alleles for psoriatic arthritis among patients with psoriasis. Ann Rheum Dis 2012; 71:50-5.
2. Winchester R, Minevich G, Steshenko V, Kirby B, Kane D, Greenberg D A, et al. HLA associations reveal genetic heterogeneity in psoriatic arthritis and in the psoriasis phenotype. Arthritis Rheum 2012; 64:1134-44.
3. Cua D J, Sherlock J P. Autoimmunity's collateral damage: Gut microbiota strikes 'back'. Nat Med 2011; 17:1055-6.
4. Van Praet L, Van den Bosch F, Mielants H, Elewaut D. Mucosal inflammation in spondylarthritides: past, present, and future. Curr Rheumatol Rep 2011; 13:409-15.
5. Sherlock J P, Joyce-Shaikh B, Turner S P, Chao C C, Sathe M, Grein J, et al. IL-23 induces spondyloarthropathy by acting on ROR-gammat+ CD3+CD4-CD8-entheseal resident T cells. Nat Med 2012; 18:1069-76.
6. Van Praet L, Van den Bosch F E, Jacques P, Carron P, Jans L, Colman R, et al. Microscopic gut inflammation in axial spondyloarthritis: a multiparametric predictive model. Ann Rheum Dis 2013; 72:414-7.
7. Rath H C, Herfarth H H, Ikeda J S, Grenther W B, Hamm T E, Jr., Balish E, et al. Normal luminal bacteria, especially *Bacteroides* species, mediate chronic colitis, gastritis, and arthritis in HLA-B27/human beta2 microglobulin transgenic rats. J Clin Invest 1996; 98:945-53.
8. Ruutu M, Thomas G, Steck R, gli-Esposti M A, Zinkernagel M S, Alexander K, et al. beta-glucan triggers spondylarthritis and Crohn's disease-like ileitis in SKG mice. Arthritis Rheum 2012; 64:2211-22.
9. Orchard T R, Wordsworth B P, Jewell D P. Peripheral arthropathies in inflammatory bowel disease: their articular distribution and natural history. Gut 1998; 42:387-91.
10. Scarpa R, Manguso F, D'Arienzo A, D'Armiento F P, Astarita C, Mazzacca G, et al. Microscopic inflammatory changes in colon of patients with both active psoriasis and psoriatic arthritis without bowel symptoms. J Rheumatol 2000; 27:1241-6.
11. Li W Q, Han J L, Chan A T, Qureshi A A. Psoriasis, psoriatic arthritis and increased risk of incident Crohn's disease in U S women. Ann Rheum Dis 2013; 72:1200-5.
12. Scher J U, Sczesnak A, Longman R S, SegataN, Ubeda C, Bielski C, et al. Expansion of intestinal Prevotella copri correlates with enhanced susceptibility to arthritis. Elife 2013; 2:e01202.
13. Scher J U, Ubeda C, Equinda M, Khanin R, Buischi Y, Viale A, et al. Periodontal disease and the oral microbiota in new-onset rheumatoid arthritis. Arthritis Rheum 2012; 64:3083-94.
14. Sheneman L, Evans J, Foster J A. Clearcut: a fast implementation of relaxed neighbor joining. Bioinformatics 2006; 22:2823-4.
15. Nielsen O H, Gionchetti P, Ainsworth M, Vainer B, Campieri M, Borregaard N, et al. Rectal dialysate and fecal concentrations of neutrophil gelatinase-associated lipocalin, interleukin-8, and tumor necrosis factor-alpha in ulcerative colitis. Am J Gastroenterol 1999; 94:2923-8.
16. Segata N, Izard J, Waldron L, Gevers D, Miropolsky L, Garrett W S, et al. Metagenomic biomarker discovery and explanation. Genome Biol 2011; 12:R60.
17. Scurati M. Learning Bayesian Networks with the bnlearn R Package. Journal of Statistical Software 2010; 35(3): 1-22.
18. Mensah K A, Ritchlin C T, Schwarz E M. RANKL induces heterogeneous D C-STAMP(lo) and D C-STAMP (hi) osteoclast precursors of which the D C-STAMP(lo) precursors are the master fusogens. J Cell Physiol 2010; 223:76-83.
19. Reveille J D. Genetics of spondyloarthritis—beyond the MHC. Nat Rev Rheumatol 2012; 8:296-304.
20. Mielants H, Veys E M, Cuvelier C, De Vos M, Goemaere S, De Clercq L, et al. The evolution of spondyloarthropathies in relation to gut histology. II. Histological aspects. J Rheumatol 1995; 22:2273-8.
21. Ciccia F, Accardo-Palumbo A, Alessandro R, Rizzo A, Principe S, Peralta S, et al. Interleukin-22 and interleukin-22-producing NKp44+ natural killer cells in subclinical gut inflammation in ankylosing spondylitis. Arthritis Rheum 2012; 64:1869-78.
22. Stebbings S, Munro K, Simon M A, Tannock G, Highton J, Harmsen H, et al. Comparison of the faecal microflora of patients with ankylosing spondylitis and controls using molecular methods of analysis. Rheumatology (Oxford) 2002; 41:1395-401.
23. Manichanh C, Rigottier-Gois L, Bonnaud E, Gloux K, Pelletier E, Frangeul L, et al. Reduced diversity of faecal microbiota in Crohn's disease revealed by a metagenomic approach. Gut 2006; 55:205-11.
24. Collado M C, Derrien M, Isolauri E, de Vos W M, Salminen S. Intestinal integrity and *Akkermansia muciniphila*, a mucin-degrading member of the intestinal microbiota present in infants, adults, and the elderly. Appl Environ Microbiol 2007; 73:7767-70.
25. Arumugam M, Raes J, Pelletier E, Le Paslier D, Yamada T, Mende D R, et al. Enterotypes of the human gut microbiome. Nature 2011; 473(7346):174-80.
26. Png C W, Linden S K, Gilshenan K S, Zoetendal E G, McSweeney C S, Sly L I, et al. Mucolytic bacteria with increased prevalence in IBD mucosa augment in vitro utilization of mucin by other bacteria. Am J Gastroenterol 2010; 105:2420-8.
27. Vigsnaes L K, Brynskov J, Steenholdt C, Wilcks A, Licht T R. Gram-negative bacteria account for main differences between faecal microbiota from patients with ulcerative colitis and healthy controls. Benef Microbes 2012; 3:287-97.
28. Rajilic-Stojanovic M, Shanahan F, Guarner F, de Vos W M. Phylogenetic analysis of dysbiosis in ulcerative colitis during remission. Inflamm Bowel Dis 2013; 19:481-8.
29. Willing B P, Dicksved J, Halfvarson J, Andersson A F, Lucio M, Zheng Z, et al. A pyrosequencing study in twins shows that gastrointestinal microbial profiles vary with inflammatory bowel disease phenotypes. Gastroenterology 2010; 139:1844-54.
30. Morgan X C, Tickle T L, Sokol H, Gevers D, Devaney K L, Ward D V, et al. Dysfunction of the intestinal microbiome in inflammatory bowel disease and treatment. Genome Biol 2012; 13:R79.
31. Joossens M, Huys G, Cnockaert M, De Preter V, Verbeke K, Rutgeerts P, et al. Dysbiosis of the faecal microbiota in patients with Crohn's disease and their unaffected relatives. Gut 2011; 60:631-7.
32. Smith P M, Howitt M R, Panikov N, Michaud M, Gallini C A, Bohlooly Y, et al. The microbial metabolites, short-chain fatty acids, regulate colonic Treg cell homeostasis. Science 2013; 341(6145):569-73.
33. Garner C E, Smith S, de Lacy C B, White P, Spencer R, Probert C S, et al. Volatile organic compounds from feces and their potential for diagnosis of gastrointestinal disease. FASEB J 2007; 21:1675-88.
34. De Preter V, Machiels K, Joossens M, Arijs I, Matthys C, Vermeire S, et al. Faecal metabolite profiling identifies medium-chain fatty acids as discriminating compounds in IBD. Gut 2014. [Epub ahead of print]
35. Liberato M V, Nascimento A S, Ayers S D, Lin J Z, Cvoro A, Silveira R L, et al. Medium chain fatty acids are selective peroxisome proliferator activated receptor (PPAR) gamma activators and pan-PPAR partial agonists. PLoS One 2012; 7(5):e36297.
36. Bassaganya-Riera J, Viladomiu M, Pedragosa M, De S C, Carbo A, Shaykhutdinov R, et al. Probiotic bacteria produce conjugated linoleic acid locally in the gut that targets macrophage PPAR gamma to suppress colitis. PLoS One 2012; 7(2):e31238.
37. Bassaganya-Riera J, Hontecillas R, Horne W T, Sandridge M, Herfarth H H, Bloomfeld R, et al. Conjugated linoleic acid modulates immune responses in patients with mild to moderately active Crohn's disease. Clin Nutr 2012; 31(5):721-7.
38. Chandran V, Cook R J, Edwin J, Shen H, Pellett F J, Shanmugarajah S, et al. Soluble biomarkers differentiate patients with psoriatic arthritis from those with psoriasis without arthritis. Rheumatology (Oxford) 2010; 49:1399-405.
39. Xue Y, Jiang L, Cheng Q, Chen H, Yu Y, Lin Y, et al. Adipokines in psoriatic arthritis patients: the correlations with osteoclast precursors and bone erosions. PLoS One 2012; 7(10):e46740.
40. Ritchlin C T, Haas-Smith S A, Li P, Hicks D G, Schwarz E M. Mechanisms of TNF-alpha- and RANKL-mediated osteoclastogenesis and bone resorption in psoriatic arthritis. J Clin Invest 2003; 111:821-31.
41. Toberer F, Sykora J, Gottel D, Ruland V, Hartschuh W, Enk A, et al. Tissue microarray analysis of RANKL in cutaneous lupus erythematosus and psoriasis. Exp Dermatol 2011; 20:600-2.
42. Knoop K A, Kumar N, Butler B R, Sakthivel S K, Taylor R T, Nochi T, et al. RANKL is necessary and sufficient to initiate development of antigen-sampling M cells in the intestinal epithelium. J Immunol 2009; 183:5738-47.
43. Moschen A R, Kaser A, Enrich B, Ludwiczek O, Gabriel M, Obrist P, et al. The RANKL/OPG system is activated in inflammatory bowel disease and relates to the state of bone loss. Gut 2005; 54:479-87.
44. Elinav E, Strowig T, Kau A L, Henao-Mejia J, Thaiss C A, Booth C J, et al. NLRP6 inflammasome regulates colonic microbial ecology and risk for colitis. Cell 2011; 145:745-57.

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

What is claimed is:

1. A method for treating a subject afflicted with psoriatic arthritis, wherein the subject afflicted with psoriatic arthritis exhibits symptoms characteristic of psoriasis of the skin selected from the group consisting of pain, swelling, or stiffness in one or more joints; joints that are red or warm to the touch; dactylitis; pain in and around the feet and ankles; and lower back pain, and the subject does not exhibit symptoms characteristic of inflammatory bowel disease selected from the group consisting of abdominal pain; vomiting; diarrhea; rectal bleeding; severe pelvic cramps; and weight loss, the method comprising administering to the subject a therapeutically effective amount of at least one medium-chain fatty acid or an ester/salt thereof or a composition thereof selected from hexanoic acid and heptanoic acid or an ester/salt thereof, wherein the at least one medium-chain fatty acid or an ester/salt thereof or composition thereof is administered orally or anally, wherein the subject afflicted with psoriatic arthritis has decreased bacterial diversity of gut microbiota, and wherein administering the therapeutically effective amount of the at least one medium-chain fatty acid or an ester/salt thereof or composition thereof treats the subject afflicted with psoriatic arthritis.

2. The method of claim 1, wherein the at least one medium-chain fatty acid is hexanoic acid or heptanoic acid.

3. The method of claim 1, wherein the at least one medium-chain fatty acid or an ester/salt thereof or composition thereof is administered anally into at least one of the terminal ileum and right colon.

4. The method of claim 1, wherein the decreased bacterial diversity of gut microbiota is determined by isolating a fecal sample from the subject and processing the fecal sample to generate a fecal bacterial sample; and analyzing microbiota diversity in the fecal bacterial sample using nucleic acid sequencing.

5. The method of claim 4, wherein the nucleic acid sequencing is shotgun sequencing.

6. The method of claim 1, wherein the subject meets three or more points from the ClASsification of Psoriatic ARthritis (CASPAR) criteria, including: (1) the presence of psoriasis (current, history of, or family history of), (2) psoriatic nail dystrophy, (3) a negative rheumatoid factor (RF) test result, (4) dactylitis (history of or current), and (5) radiographic evidence of juxta-articular new bone formation.

* * * * *

UNITED STATES PATENT AND TRADEMARK OFFICE
CERTIFICATE OF CORRECTION

PATENT NO. : 10,226,443 B2
APPLICATION NO. : 14/885084
DATED : March 12, 2019
INVENTOR(S) : Jose U. Scher It is certified that error appears in the above-identified patent and that said Letters Patent is hereby corrected as shown below:

In the Specification

At Column 1, Line 14, "GOVERNMENTAL SUPPORT", should read:
-- This invention was made with government support under grant numbers AR058986 and K23 AR064318 awarded by The National Institutes of Health. The government has certain rights in the invention. --

Signed and Sealed this
First Day of November, 2022

Katherine Kelly Vidal
*Director of the United States Patent and Trademark Office*